United States Patent [19]
Varasi et al.

[11] Patent Number: 5,637,596
[45] Date of Patent: Jun. 10, 1997

[54] AZABICYCLOALKYL DERIVATIVES OF IMIDAZO[1,5-A]INDOL-3-ONE AND PROCESS FOR THEIR PREPARATION

[75] Inventors: Mario Varasi, Milan; Franco Heidempergher, Parabiago; Carla Caccia, Gallarate; Patricia Salvati, Arese, all of Italy

[73] Assignee: Pharmacia S.p.A., Milan, Italy

[21] Appl. No.: 578,548

[22] PCT Filed: May 2, 1995

[86] PCT No.: PCT/EP95/01652

§ 371 Date: Jan. 24, 1996

§ 102(e) Date: Jan. 24, 1996

[87] PCT Pub. No.: WO95/32209

PCT Pub. Date: Nov. 30, 1995

[30] Foreign Application Priority Data

May 24, 1994 [GB] United Kingdom ............... 9410441

[51] Int. Cl.⁶ ............... A61K 31/46; C07D 453/02
[52] U.S. Cl. ............... 514/305; 514/304; 546/126; 546/133
[58] Field of Search ............... 514/304, 305; 546/126, 133

[56] References Cited

U.S. PATENT DOCUMENTS

| | | | |
|---|---|---|---|
| 3,565,902 | 2/1971 | Wright et al. | 546/199 |
| 5,364,854 | 11/1994 | Varasi et al. | 514/230.2 |

FOREIGN PATENT DOCUMENTS

| | | |
|---|---|---|
| 0505778 | 9/1992 | European Pat. Off. . |
| WO93/15073 | 8/1993 | WIPO . |
| 9325555 | 12/1993 | WIPO . |

OTHER PUBLICATIONS

Bermudez et al, *Journal of Medicinal Chemistry*, "'5-Hydroxytryptamine (5-HT3) receptor antagonists. 2 ...'", vol. 33, No. 7, pp. 1929–1932, 1990.

*Primary Examiner*—C. Warren Ivy
*Assistant Examiner*—Garth M. Dahlen
*Attorney, Agent, or Firm*—Nikaido Marmelstein Murray & Oram LLP

[57] ABSTRACT

Novel 5-HT$_3$ receptor antagonist compounds having the general formula (I)

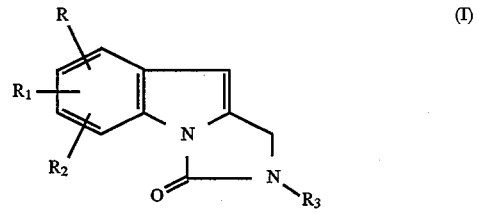

wherein
each of R, R$_1$ and R$_2$, which may be the same or different, is hydrogen, halogen, hydroxy, cyano, C$_1$–C$_6$ alkyl, CF$_3$, C$_1$–C$_6$ alkoxy, C$_1$–C$_6$ alkylthio, formyl, C$_2$–C$_6$ alkanoyl, carboxy, C$_1$–C$_6$ alkoxy-carbonyl, nitro, —N(R$_4$ R$_5$) in which each of R$_4$ and R$_5$ independently is hydrogen, C$_1$–C$_6$ alkyl, formyl or C$_2$–C$_6$ alkanoyl; or a (R$_6$ R$_7$)N—SO$_2$ group, in which each of R$_6$ and R$_7$ independently is hydrogen or C$_1$–C$_6$ alkyl;

R$_3$ is a group a)

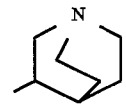

or b)

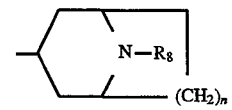

wherein
n is an integer of 1 or 2 and R$_8$ is hydrogen, C$_1$–C$_6$ alkyl unsubstituted or substituted by phenyl, C$_2$–C$_4$ alkenyl, C$_2$–C$_4$ alkynyl, formyl or C$_2$–C$_6$ alkanoyl; and the pharmaceutically acceptable salts thereof, are provided.

11 Claims, No Drawings

AZABICYCLOALKYL DERIVATIVES OF IMIDAZO[1,5-A]INDOL-3-ONE AND PROCESS FOR THEIR PREPARATION

This application is a 371 of PCT/EP95/01652 filed May 2, 1995.

The present invention relates to new derivatives of 2-azabicycloalkyl-1,2-dihydro-imidazo[1,5-a]indol-3-one, to a process for their preparation, to pharmaceutical compositions containing them and to their use as therapeutic agents.

The present invention provides novel compounds having the general formula (I)

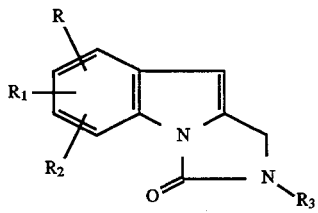

wherein
each of R, $R_1$ and $R_2$, which may be the same or different, is hydrogen, halogen, hydroxy, cyano, $C_1$–$C_6$ alkyl, $CF_3$, $C_1$–$C_6$ alkoxy, $C_1$–$C_6$ alkylthio, formyl, $C_2$–$C_6$ alkanoyl, carboxy, $C_1$–$C_6$ alkoxy-carbonyl, nitro, —N($R_4$ $R_5$) in which each of $R_4$ and $R_5$ independently is hydrogen, $C_1$–$C_6$ alkyl, formyl or $C_2$–$C_6$ alkanoyl; or a ($R_6$ $R_7$)N—$SO_2$ group, in which each of $R_6$ and $R_7$ independently is hydrogen or $C_1$–$C_6$ alkyl;

$R_3$ is a group a)

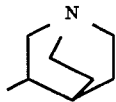

or b)

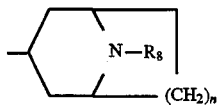

wherein
n is an integer of 1 or 2 and $R_8$ is hydrogen, $C_1$–$C_6$ alkyl unsubstituted or substituted by phenyl, $C_2$–$C_4$ alkenyl, $C_2$–$C_4$ alkynyl, formyl or $C_2$–$C_6$ alkanoyl; and the pharmaceutically acceptable salts thereof.

The formula reported above for the compounds according to the present invention includes all the possible isomers, in particular stereoisomers, as well as their mixtures. In the compounds of the invention wherein the substituent $R_3$ is a group a), as defined above, such group may be in the R- or S-configuration, or in mixtures thereof.

Similarly when the substituent $R_3$ is a group b), as defined above, such group may be in the endo- or exo-configuration or mixtures thereof, the endo being the preferred.

The invention includes within its scope the metabolites and the metabolic precursors or bio-precursors (otherwise known as pro-drugs) of the compounds of formula (I).

Namely the invention includes compounds which have a different formula to formula (I) above but which nevertheless upon administration to a human being are converted directly or indirectly in vivo into a compound of formula (I).

A halogen atom may be a fluorine, chlorine, bromine or iodine atom, preferably it is chlorine or bromine. The alkyl, alkenyl, alkynyl, alkoxy and alkylthio group may be a branched or straight chain groups.

A $C_1$–$C_6$ alkyl group is preferably a $C_1$–$C_4$ alkyl group, e.g. methyl, ethyl, propyl, isopropyl, butyl, sec.butyl or tert.butyl, in particular methyl or ethyl.

A $C_1$–$C_6$ alkoxy group is preferably a $C_1$–$C_4$ alkoxy group e.g. methoxy, ethoxy, propoxy, isopropoxy and butoxy, preferably methoxy and ethoxy.

A $C_1$–$C_6$ alkylthio group is preferably a $C_1$–$C_4$ alkylthio group, e.g. methylthio, ethylthio, propylthio and butylthio, in particular methylthio.

A $C_2$–$C_4$ alkenyl group is preferably allyl.

A $C_2$–$C_4$ alkynyl group is preferably propargyl.

A $C_2$–$C_6$ alkanoyl group is e.g. a $C_2$–$C_4$ alkanoyl group, in particular acetyl and propionyl.

Pharmaceutically acceptable salts of the compounds of formula (I) include acid addition salts, with inorganic acids e.g. nitric, hydrochloric, hydrobromic, sulphuric, perchloric and phosphoric acid, or organic acids e.g. acetic, propionic, glycolic, lactic, oxalic, malonic, malic, maleic, tartaric, citric, benzoic, cinnamic, fumaric, mandelic and salicylic acid.

Preferred compounds of the invention are the compounds of formula (I) wherein each of R, $R_1$ and $R_2$, which may be the same or different, is hydrogen, halogen, cyano, $CF_3$, $C_1$–$C_4$ alkyl, $C_1$–$C_4$ alkylthio, $C_1$–$C_4$ alkoxy or —N($R_4$ $R_5$) in which each of $R_4$ and $R_5$ independently is hydrogen, $C_1$–$C_4$ alkyl, formyl or $C_2$–$C_4$ alkanoyl;

$R_3$ is

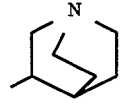

or

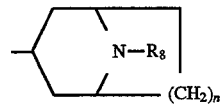

in which n is 1 or 2 and $R_8$ is $C_1$–$C_4$ alkyl; and the pharmaceutically acceptable salts thereof.

Examples of preferred compounds according to the invention are the following:

2-(1-azabicyclo[2.2.2]oct-3-yl)-1,2-dihydro-imidazo[1,5-a]indol-3-one;

2-(1-azabicyclo[2.2.2]oct-3-yl)-8-chloro-1,2-dihydro-imidazo[1,5-a]indol-3-one;

2-(1-azabicyclo[2.2.2]oct-3-yl)-6-chloro-1,2-dihydro-imidazo[1,5-a]indol-3-one;

2-(1-azabicyclo[2.2.2]oct-3-yl)-6-methyl-1,2-dihydro-imidazo[1,5-a]indol-3-one;

2-(1-azabicyclo[2.2.2]oct-3-yl)-8-methyl-1,2-dihydro-imidazo[1,5-a]indol-3-one;

2-(1-azabicyclo[2.2.2]oct-3-yl)-6,8-dichloro-1,2-dihydro-imidazo[1,5-a]indol-3-one;

2-(1-azabicyclo[2.2.2]oct-3-yl)-6,8-dimethyl-1,2-dihydro-imidazo[1,5-a]indol-3-one;

(endo)-2-(8-methyl-8-azabicyclo[3.2.1]oct-3-yl)-1,2-dihydro-imidazo[1,5-a]indol-3-one;

(endo)-2-(9-methyl-9-azabicyclo[3.3.1]non-3-yl)-1,2-dihydro-imidazo[1,5-a]indol-3-one;

and the pharmaceutically acceptable salts thereof, in particular the hydrochloride.

The compounds of the invention and the salts thereof can be obtained by a process comprising reacting a compound of formula (II)

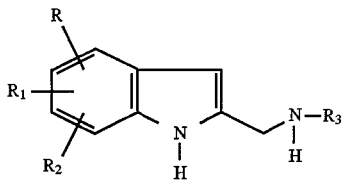

(II)

wherein

R, $R_1$, $R_2$ and $R_3$ are as defined above, with a carbonyl containing cyclizing agent and, if desired, converting a compound of formula (I) into another compound of formula (I), and/or, if desired, converting a compound of formula (I) into a pharmaceutically acceptable salt thereof, and/or, if desired, converting a salt into a free-compound, and/or, if desired, separating a mixture of isomers of a compound of formula (I) into the single isomers.

A carbonyl containing cyclizing agent, according to the invention, is e.g. an alkyl-haloformiate, typically a $C_1$–$C_4$ alkyl-haloformiate, in particular methyl chloro-formiate, N,N-carbonyldiimidazole, the latter being the preferred.

The cyclizing reaction can be carried out in an aprotic organic solvent chosen for instance from tetrahydrofuran, benzene, toluene and xylene, at reaction temperatures ranging from about 50° C. to reflux temperature and if need be under an inert, e.g. nitrogen, atmosphere.

A compound of formula (I) can be converted, if desired, into another compound of formula (I). Thus for instance a compound of formula (I) wherein one or more of R, $R_1$ and $R_2$ is amino can be converted into another compound of formula (I) wherein one or more of R, $R_1$ and $R_2$ is $C_2$–$C_6$ alkanoylamino or formylamino.

A compound of formula (I) in which one or more of R, $R_1$ and $R_2$ is carboxy can be converted into another compound of formula (I) wherein one or more of R, $R_1$ and $R_2$ is $C_1$–$C_6$ alkoxycarbonyl, and vice versa. These optional conversions can be carried out by methods known in themselves.

The optional salification of a compound of formula (I) as well as the conversion of a salt into the free compound and the separation of a mixture of isomers into the single isomers may be carried out by conventional methods.

For example the separation of a mixture of geometric isomers, e.g. endo- and exo-isomers, may be carried out by fractional crystallization from a suitable solvent or by chromatography, either column chromatography or high pressure liquid chromatography.

If desired, the separation of a mixture of isomers into the single isomers may carried out also on the intermediate products e.g. by following the above described methods and in general according to techniques well known in the art.

The compounds of formula (II) which are new and are a further object of this invention can be obtained by reacting a compound of formula (III)

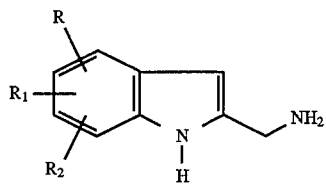

(III)

wherein R, $R_1$ and $R_2$ are as defined above, either with a compound of formula (IV) or of formula (V), or a salt thereof in particular the hydrochloride.

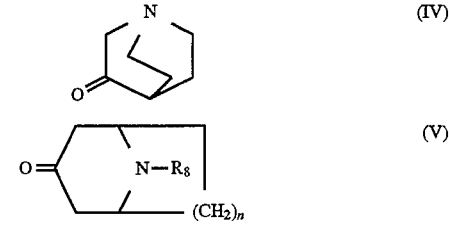

wherein $R_8$ and n are as defined above, thus obtaining a compound of formula (II) wherein $R_3$ is as defined above. The reaction of a compound of formula (III) with a compound of formula (IV) or (V) can be carried out according to known methods in the art. According to a preferred embodiment of the invention, if the reaction provides a mixture of isomers of a compound of formula (II), before submitting them to the above cyclizing reaction such mixture of isomers can be separated into the single isomers, e.g. endo- and exo-isomers, by methods well known in the art, e.g. by silica gel flash-chromatography.

The compounds of formula (III) are known or may be obtained according to known procedures as described in J. Med. Chem., 11, 1164 (1968).

The compounds of formula (IV) and (V) are well known compounds or may be obtained from known compounds and by known methods.

When in the compounds described above groups are present which need to be protected during the reactions described above, such groups can be protected in a conventional way before the reaction takes place and then deprotected. Examples of protecting groups are those employed usually in the chemistry of peptides.

The compounds of the invention are active on the serotoninergic system, in particular as $5HT_3$ receptor antagonists, as proven for example by the fact that they have been found to be active in antagonizing the von Bezold-Jarisch chemoreflex evoked by 5HT in the anesthetized rat according to the method described by Fozard J. R., Naunyn-Schmiedeberg's Arch. Pharmacol. 326, 36–44 (1984).

The following Table I reports in-vivo $5HT_3$ antagonist activity data obtained in this test for two representative compounds of the invention.

TABLE I

Inhibition of the von Bezold-Jarisch reflex elicited by 5-HT (30 µg/kg i.v.) by FCE compounds in the anesthetized rat. Values are mean ± in S.E.M. from N animals

| Compound | Dose (µg/kg i.v.) | N | % inhibition | $ED_{50}$ (50 µg/kg) (limits) |
|---|---|---|---|---|
| FCE 28837 | 100 | 6 | 88.5 | 11.8 (7.73–17.14) |
| FCE 28841 | 100 | 6 | 90.71 | 21.8 (14.3–36.2) |
| Vehicle | | | 4.42 ± 2.91 | |

*P < 0.01 vs controls (Dunnett's tests)
N = number of animals

The affinity for serotonin $5HT_3$ receptors was assessed for instance in rat entorhinal cortex using a selective radioligand $^3$H-BRL 43694 as described by Nelson and Thomas (1989).

Nelson D. R. and Thomas D. R., [$^3$H]-BRL 43694 (Granisetron), a specific ligand for $5HT_3$ binding sites in rat brain cortical membranes, Biochem. Pharmac., 38, 1693–1695, 1989.

The following Table II summarized the data obtained in this in-vitro test for two representative compounds of the invention.

TABLE II

| 5-HT$_3$ binding affinity for rat enthiorinal cortex $^3$H-BRL 43694 | |
|---|---|
| Compound | IC$_{50}$, nM |
| FCE 28837 | 10 |
| FCE 28841 | 7 |

In the tables:
FCE 28837 means: (endo)-2-(8-methyl-B-azabicyclo[3.2.1]oct-3-yl)-1,2-dihydro-imidazo[1,5-a]indol-3-one.
FCE 28841 means: 2-(1-azabicyclo[2.2.2]oct-3-yl)-1,2-dihydro-imidazo[1,5-a]indol-3-one hydrochloride.

In view of said activity, the compounds of the present invention can be useful, for example, in the treatment of CNS disorders such as, e.g., anxiety and psychosis, and/or in the treatment of gut motility disorders, and/or emesis.

In view of the above activity, the compounds of the invention can be also useful as, for example, anti-migraine or anti-drug addiction agents, or as cognition activators.

The dosage levels suitable for administration to adult humans of the compounds of the invention, either for prophylaxis or therapeutic treatment, may range from about 0.010 to about 20 mg/kg of body weight, depending on the chosen route of administration, on the particular compound chosen, on the particular patient under treatment and also on the nature and severity of the disorder.

For instance the compound of the invention 2-(1-azabicyclo[2.2.2]oct-3-yl)-1,2-dihydro-imidazo[1,5-a]indol-3-one is suitable administered orally at a dosage in this range.

Preferably the compounds may be, e.g., administered in single or divided doses such that the total daily dosage falls within the range of about 0.020 to about 10 mg/kg per day.

Of course, these dosage regimens may be adjusted to provide the optimal therapeutic response.

The compounds of the invention can be administered in a variety of dosage forms, e.g. orally, in the form of tablets, capsules, sugar, or film coated tablets, liquid solutions or suspensions.

The invention includes pharmaceutical compositions comprising a compound of the invention in association with a pharmaceutically acceptable excipient (which can be a carrier or diluent).

The nature of the pharmaceutical compositions containing the compounds of this invention in association with pharmaceutically acceptable carriers or diluents will, of course, depend upon the desired route of administration. The compositions may be formulated in the conventional manner with the usual ingredients. For example, the compounds of the invention may be administered in the form of aqueous or oily solutions, or suspensions, tablets, pills, gelatine capsules, syrups, drops or suppositories.

Thus, for oral administration, the pharmaceutical composition containing the compounds of this invention are preferably tablets, pills or gelatin capsules which contain the active substance together with diluents, such as lactose, dextrose, sucrose, mannitol, sorbitol, cellulose; lubrificants, for instance silica, talc, stearic acid, magnesium or calcium stearate, and/or polyethylene glycols; or they may also contain binders, such as starches, gelatine, methylcellulose, carboxy-methylcellulose, gum-arabic, tragacanth, polyvinyl-pyrrolidone; disaggregating agents, such as starches, alginic acid, alginates, sodium starch glycolate; effervescing mixtures; dyestuffs; sweeteners; wetting agents, such as lecithin, polysorbates, laurylsulphates; and in general, non-toxic and pharmacologically inactive substances used in pharmaceutical formulations. Said pharmaceutical preparations may be manufactured in known manner, for example by means of mixing, granulating, tabletting, sugar-coating, or film-coating processes, the liquid dispersions for oral administration may be e.g. syrups, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lindocaine hydrochloride.

The solutions for intravenous injection or infusion may contain as carrier, for example, sterile water or preferably they may be in the form of sterile aqueous isotonic saline solutions.

The suppositories may contain together with the active compound a pharmaceutically acceptable carrier e.g. cocoabutter, polyethylene glycol, a polyoxyethylene sorbitan fatty acid ester surfactant or lecithin.

The following examples illustrate but do not limit the present invention.

EXAMPLE 1

2-[(1-azabicyclo[2.2.2]oct-3-yl)aminomethyl]-1H-indole

To a stirred solution of 2-aminomethyl-1H-indole (5 g; 0.034 moles) in 75 ml of anhydrous methanol kept under nitrogen atmosphere, 3-quinuclidinone hydrochloride (5.53 g; 0.0342 moles) is added. The pH is adjusted to pH 6 by addition of glacial acetic acid.

Sodium cyanoborohydride (4.3 g; 0.0684 moles) is added in three portions. The reaction mixture is refluxed for 10 hours, cooled and then filtered. After evaporation to dryness the residue is taken up with water, basified with 20% sodium hydroxide solution and extracted three times with ethyl acetate. The organic layer is washed with brine, dried over anhydrous sodium sulfate and, after filtration, evaporated to dryness. The residue is purified by silica gel flash-chromatograph, (ethyl acetate-methanol-30% ammonium hydroxide, 170:30:3 as eluant) to give the title product as a cream solid (4.5 g); m.p. 169°–172° C. dec.

$C_{16}H_{21}N_3$ required=C: 75.25 H: 8.29 N: 16.46 found=C: 74.88 H: 8.40 N: 16.23

By proceeding analogously the following compounds can be prepared either as free bases or as dihydrochloride salts thereof:

2-[(1-azabicyclo[2.2.2]oct-3-yl)aminomethyl]-1H-4-chloro-indole;

2-[(1-azabicyclo[2.2.2]oct-3-yl)aminomethyl]-1H-6-chloro-indole;

2-[(1-azabicyclo[2.2.2]oct-3-yl)aminomethyl]-1H-4-methyl-indole;

2-[(1-azabicyclo[2.2.2]oct-3-yl)aminomethyl]-1H-6-methyl-indole;

2-[(1-azabicyclo[2.2.2]oct-3-yl)aminomethyl]-1H-4,6-dichloro-indole; and

2-[(1-azabicyclo[2.2.2]oct-3-yl)aminomethyl]-1H-4,6-dimethyl-indole.

EXAMPLE 2

2-[(endo-8-methyl-8-azabicyclo[3.2.1]oct-3-yl)-aminomethyl]-1H-indole; 2-[(exo-8-8-azabicyclo[3.2.1]oct-3-yl)aminomethyl]-1H-indole To a stirred solution of 2-aminomethyl-1H-indole (4.35 g; 0.0298 moles) in 60 ml of anhydrous methanol kept under nitrogen atmosphere, tropinone (4.14 g; 0.0298 moles) is added. The pH is adjusted to pH 6 by addition of glacial acetic acid.

Sodium cyanoborohydride (3.74 g; 0.0595 moles) is added in three portions. The reaction mixture is refluxed 8 hours, cooled and filtered. After evaporation the residue is taken up with water, basified with 20% sodium hydroxide and extracted three times with ethyl acetate. The organic layer is washed with brine, dried over anhydrous sodium sulfate and, after filtration, evaporated to dryness. The residue is purified by silica gel flash-chromatography (methylene-chloride-methanol-30% ammonium hydroxide, 180:20:2 as eluant) to give a mixture of the title endo and exo products as an oil (4.8 g).

$C_{17}H_{23}N_3$ required=C: 75.80 H: 8.61 N: 15.60 found=C: 75.49 H: 8.83 N: 15.31

By proceeding analogously the following mixture of endo and exo products can be prepared:

2-[(8-methyl-8-azabicyclo[3.2.1]oct-3-yl)aminomethyl-1H-4-chloro-indole;

2-[(8-methyl-8-azabicyclo[3.2.1]oct-3-yl)aminomethyl]-1H-6-chloro-indole;

2-[(8-methyl-8-azabicyclo[3.2.1]oct-3-yl)aminomethyl]-1H-4-methyl-indole;

2-[(8-methyl-8-azabicyclo[3.2.1]oct-3-yl)aminomethyl]-1H-6-methyl-indole;

2-[(8-methyl-8-azabicyclo[3.2.1]oct-3-yl)aminomethyl]-1H-4,6-dichloro-indole; and 2-[(8-methyl-8-azabicyclo[3.2.1]oct-3-yl)aminomethyl]-1H-4,6-dimethyl-indole.

EXAMPLE 3

By proceeding analogously to the procedure described in Example 2, starting from 2-aminomethyl-1H-indole and 9-methyl-9-azabicyclo[3.3.1]nonan-3-one-hydrochloride the compound 2-[(9-methyl-9-azabicyclo[3.3.1]non-3-yl)amino-methyl]-1H-indole can be obtained as a mixture of endo and exo products as an oil.

$C_{18}H_{25}N_3$ required=C: 76.28 H: 8.89 N: 14.83 found=C: 75.89 H: 9.11 N: 14.51

Analogously the following compounds as a mixture of endo and exo products can be prepared:

2-[(9-methyl-9-azabicyclo[3.3.1]non-3-yl)aminomethyl]-1H-4-chloro-indole;

2-[(9-methyl-9-azabicyclo[3.3.1]non-3-yl)aminomethyl]-1H-6-chloro-indole;

2-[(9-methyl-9-azabicyclo[3.3.1]non-3-yl)aminomethyl]-1H-4-methyl-indole;

2-[(9-methyl-9-azabicyclo[3.3.1]non-3-yl)aminomethyl]-1H-6-methyl-indole;

2-[(9-methyl-9-azabicyclo[3.3.1]non-3-yl)aminomethyl]-1H-4,6-dichloro-indole; and 2-[(9-methyl-9-azabicyclo[3.3.1]non-3-yl)aminomethyl]-1H-4,6-dimethyl-indole.

EXAMPLE 4

2-(1-azabicyclo[2.2.2]oct-3-yl)-1,2-dihydro-imidazo[1,5-a]indol-3-one hydrochloride hydrate To a stirred solution of 2-[(1-azabicyclo[2.2.2]oct-3-yl)aminomethyl]-1H-indole (3.18 g; 0.0124 moles) in anhydrous tetrahydrofuran (20 ml), N,N-carbonyldiimidazole (2.63 g; 0.0162 moles) is added.

The reaction mixture is refluxed for 4 hours under nitrogen atmosphere. After evaporation, the residue is taken up with ethyl acetate, washed with water and dried over anhydrous sodium sulfate. After filtration and evaporation to dryness, the product is dissolved in absolute ethanol and an excess of a solution of hydrochloric acid in ethanol is added. Diethyl ether is added, the crude salt is collected by filtration and recrystallized from absolute ethanol to yield 2.1 g of the title product as a white solid; m.p. 275.5°–280.5° C.
$C_{17}H_{19}N_3O.HCl.H_2O$ required=C: 60.80 H: 6.60 N: 12.51 Cl: 10.56 found=C: 60.44 H: 6.58 N: 12.53 Cl: 10.32

By proceeding analogously the following compounds can be obtained as hydrochloride:

2-(1-azabicyclo[2.2.2]oct-3-yl)-8-chloro-1,2-dihydro-imidazo[1,5-a]indol-3-one;

2-(1-azabicyclo[2.2.2]oct-3-yl)-6-chloro-1,2-dihydro-imidazo[1,5-a]indol-3-one;

2-(1-azabicyclo[2.2.2]oct-3-yl)-6-methyl-1,2-dihydro-imidazo[1,5-a]indol-3-one;

2-(1-azabicyclo[2.2.2]oct-3-yl)-8-methyl-1,2-dihydro-imidazo[1,5-a]indol-3-one;

2-(1-azabicyclo[2.2.2]oct-3-yl)-6,8-dichloro-1,2-dihydro-imidazo[1,5-a]indol-3-one; and 2-(1-azabicyclo[2.2.2]oct-3-yl)-6,8-dimethyl-1,2-dihydro-imidazo[1,5-a]indol-3-one.

EXAMPLE 5

(endo)-2-(8-methyl-8-azabicyclo[3.2.1]oct-3-yl)-1,2-dihydro-imidazo[1,5-a]indol-3-one;(exo)-2-(8-methyl-8-azabicyclo[3.2.1]oct-3-yl)-1,2-dihydro-imidazo[1,5-a]-indol-3-one To a stirred solution of a mixture of 2-[(endo-8-methyl-8-azabicyclo[3.2.1]oct-3-yl)aminomethyl]-1H-indole and 2-[(exo-8-methyl-8-azabicyclo[3.2.1]oct-3-yl)aminomethyl]-1H-indole (4.7 g; 0.0174 moles) in 30 ml of anhydrous tetrahydrofuran, N,N-carbonyldiimidazole (3.76 g; 0.0232 moles) is added.

The reaction mixture is refluxed for 8 hours under nitrogen atmosphere. After evaporation, the residue is taken up with ethyl acetate, washed with water and dried over anhydrous sodium sulfate. After filtration and evaporation to dryness, the mixture is purified by silica gel flash-chromatography (ethyl acetate: methanol:triethylamine, 80:10:3 as eluant) to obtain the title (endo) and (exo) products.

The (endo) product is triturated with dry diethyl ether to give 1.4 g of a white solid; m.p. 193°–195.5° C.

$C_{18}H_{21}N_3O$ required=C: 73.19 H: 7.17 N: 14.23 found=C: 73.26 H: 7.25 N: 14.24

Analogously the (exo) product is obtained as a white solid (0.92 g); m.p. 188.5°–192° C. $C_{18}H_{21}N_3O$ required=C: 73.19 H: 7.17 N: 14.23 found=C: 73.12 H: 7.24 N: 14.22

By proceeding analogously the following compounds can be prepared either as a free base or as hydrochloride salt thereof:

(endo)-2-(8-methyl-8-azabicyclo[3.2.1]oct-3-yl)-8-chloro-1,2-dihydro-imidazo[1,5-a]indol-3-one;

(exo)-2-(8-methyl-8-azabicyclo[3.2.1]oct-3-yl)-8-chloro-1,2-dihydro-imidazo[1,5-a]indol-3-one;
(endo)-2-(8-methyl-8-azabicyclo[3.2.1]oct-3-yl)-6-chloro-1,2-dihydro-imidazo[1,5-a]indol-3-one;
(exo)-2-(8-methyl-8-azabicyclo[3.2.1]oct-3-yl)-6-chloro-1,2-dihydro-imidazo[1,5-a]indol-3-one;
(endo)-2-(8-methyl-8-azabicyclo[3.2.1]oct-3-yl)-8-methyl-1,2-dihydro-imidazo[1,5-a]indol-3-one;
(exo)-2-(8-methyl-8-azabicyclo[3.2.1]oct-3-yl)-6-methyl-1,2-dihydro-imidazo[1,5-a]indol-3-one;
(endo)-2-(8-methyl-8-azabicyclo[3.2.1]oct-3-yl)-6,8-dichloro-1,2-dihydro-imidazo[1,5-a]indol-3-one;
(exo)-2-(8-methyl-8-azabicyclo[3.2.1]oct-3-yl)-6,8-dichloro-1,2-dihydro-imidazo[1,5-a]indol-3-one;
(endo)-2-(8-methyl-8-azabicyclo[3.2.1]oct-3-yl)-6,8-dimethyl-1,2-dihydro-imidazo[1,5-a]indol-3-one;
(exo)-2-(8-methyl-8-azabicyclo[3.2.1]oct-3-yl)-6,8-dimethyl-1,2-dihydro-imidazo[1,5-a]indol-3-one;
(endo)-2-(9-methyl-9-azabicyclo[3.3.1]non-3-yl)-1,2-dihydro-imidazo[1,5-a]indol-3-one m.p. 199.5°–201.5° C.;
(exo)-2-(9-methyl-9-azabicyclo[3.3.1]non-3-yl)-1,2-dihydro-imidazo[1,5-a]indol-3-one m.p. 183°–186.5° C.;
(endo)-2-(9-methyl-9-azabicyclo[3.3.1]non-3-yl)-8-chloro-1,2-dihydro-imidazo[1,5-a]indol-3-one;
(exo)-2-(9-methyl-9-azabicyclo[3.3.1]non-3-yl)-8-chloro-1,2-dihydro-imidazo[1,5-a]indol-3-one;
(endo)-2-(9-methyl-9-azabicyclo[3.3.1]non-3-yl)-6-chloro-1,2-dihydro-imidazo[1,5-a]indol-3-one;
(exo)-2-(9-methyl-9-azabicyclo[3.3.1]non-3-yl)-6-chloro-1,2-dihydro-imidazo[1,5-a]indol-3-one;
(endo)-2-(9-methyl-9-azabicyclo[3.3.1]non-3-yl)-8-methyl-1,2-dihydro-imidazo[1,5-a]indol-3-one;
(exo)-2-(9-methyl-9-azabicyclo[3.3.1]non-3-yl)-8-methyl-1,2-dihydro-imidazo[1,5-a]indol-3-one;
(endo)-2-(9-methyl-9-azabicyclo[3.3.1]non-3-yl)-6-methyl-1,2-dihydro-imidazo[1,5-a]indol-3-one;
(exo)-2-(9-methyl-9-azabicyclo[3.3.1]non-3-yl)-6-methyl-1,2-dihydro-imidazo[1,5-a]indol-3-one;
(endo)-2-(9-methyl-9-azabicyclo[3.3.1]non-3-yl)-6,8-dichloro-1,2-dihydro-imidazo[1,5-a]indol-3-one;
(exo)-2-(9-methyl-9-azabicyclo[3.3.1]non-3-yl)-6,8-dichloro-1,2-dihydro-imidazo[1,5-a]indol-3-one;
(endo)-2-(9-methyl-9-azabicyclo[3.3.1]non-3-yl)-6,8-dimethyl-1,2-dihydro-imidazo[1,5-a]indol-3-one;
(exo)-2-(9-methyl-9-azabicyclo[3.3.1]non-3-yl)-6,8-dimethyl-1,2-dihydro-imidazo[1,5-a]indol-3-one;
(exo)-2-(8-methyl-8-azabicyclo[3.2.1]oct-3-yl)-8-methyl-1,2-dihydro-imidazo[1,5-a]indol-3-one; and
(endo)-2-(8-methyl-8-azabicyclo[3.2.1]oct-3-yl)-6-methyl-1,2-dihydro-imidazo[1,5-a]indol-3-one.

EXAMPLE 6

Tablets each weighing 150 mg and containing 60 mg of the active substance can be manufactured by blending and compressing the following ingredients:

| | |
|---|---|
| 2-(1-azabicyclo[2.2.2]oct-3-yl)-1,2-dihydro-imidazo[1,5-a]indol-3-one hydrochloride | 60 mg |
| Starch | 50 mg |
| Cellulose microcrystalline | 30 mg |
| Polyvinylpyrrolidone | 5 mg |
| Sodium carboxymethyl starch | 4.5 mg |
| Magnesium stearate | 0.5 mg |

EXAMPLE 7

Capsules, each dosed at 200 mg and containing 80 mg of the active substance can be prepared as follows:

| | |
|---|---|
| 2-(1-azabicyclo[2.2.2]oct-3-yl)-1,2-dihydro-imidazo[1,5-a]indol-3-one hydrochloride | 80 mg |
| Corn starch | 60 mg |
| Cellulose microcrystalline | 59 mg |
| Magnesium stearate | 1 mg |

This formulation can be encapsulated in two piece hard gelatin capsules and dosed at 200 mg for each capsule.

We claim:

1. A compound of formula (I)

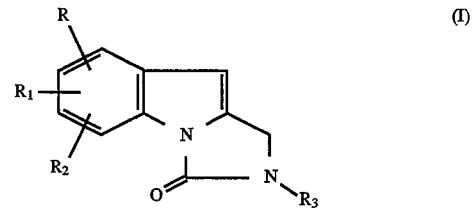

wherein each of R, $R_1$ and $R_2$, which may be the same or different, is hydrogen, halogen, hydroxy, cyano, $C_1$–$C_6$ alkyl, $CF_3$, $C_1$–$C_6$ alkoxy, $C_1$–$C_6$ alkylthio, formyl, $C_2$–$C_6$ alkanoyl, carboxy, $C_1$–$C_6$ alkoxy-carbonyl, nitro, —N($R_4$ $R_5$) in which each of $R_4$ and $R_5$ independently is hydrogen, $C_1$–$C_6$ alkyl, formyl or $C_2$–$C_6$ alkanoyl; or a ($R_6$ $R_7$)N—$SO_2$ group, in which each of $R_6$ and $R_7$ independently is hydrogen or $C_1$–$C_6$ alkyl;

$R_3$ is a group a)

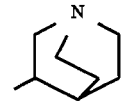

or b)

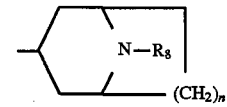

wherein n is an integer of 1 or 2 and $R_8$ is hydrogen, $C_1$–$C_6$ alkyl unsubstituted or substituted by phenyl, $C_2$–$C_4$ alkenyl, $C_2$–$C_4$ alkynyl, formyl or $C_2$–$C_6$ alkanoyl; and the pharmaceutically acceptable salts thereof.

2. A compound of formula (I), according to claim 1, wherein each of R, $R_1$ and $R_2$, which may be the same or different, is hydrogen, halogen, cyano, $CF_3$, $C_1$–$C_4$ alkyl, $C_1$–$C_4$ alkylthio, $C_1$–$C_4$ alkoxy or —N($R_4R_5$) in which each of $R_4$ and $R_5$ independently is hydrogen, $C_1$–$C_4$ alkyl, formyl or $C_2$–$C_4$ alkanoyl;

$R_3$ is

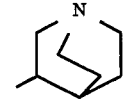

or

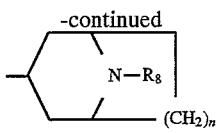

in which n is 1 or 2 and $R_8$ is $C_1$–$C_4$ alkyl; and the pharmaceutically acceptable salts thereof.

3. A compound selected from the group consisting of:
2-(1-azabicyclo[2.2.2]oct-3-yl)-1,2-dihydro-imidazo[1,5-a]indol-3-one;
2-(1-azabicyclo[2.2.2]oct-3-yl)-8-chloro-1,2-dihydro-imidazo[1,5-a]indol-3-one;
2-(1-azabicyclo[2.2.2]oct-3-yl)-6-chloro-1,2-dihydro-imidazo[1,5-a]indol-3-one;
2-(1-azabicyclo[2.2.2]oct-3-yl)-6-methyl-1,2-dihydro-imidazo[1,5-a]indol-3-one;
2-(1-azabicyclo[2.2.2]oct-3-yl)-8-methyl-1,2-dihydro-imidazo[1,5-a]indol-3-one;
2-(1-azabicyclo[2.2.2]oct-3-yl)-6,8-dichloro-1,2-dihydro-imidazo[1,5-a]indol-3-one;
2-(1-azabicyclo[2.2.2]oct-3-yl)-6,8-dimethyl-1,2-dihydro-imidazo[1,5-a]indol-3-one;
(endo)-2-(8-methyl-8-azabicyclo[3.2.1]oct-3-yl)-1,2-dihydro-imidazo[1,5-a]indol-3-one;
(endo)-2-(9-methyl-9-azabicyclo[3.3.1]non-3-yl)-1,2-dihydro-imidazo[1,5-a]indol-3-one, or a pharmaceutically acceptable salt thereof, in particular the hydrochloride.

4. A process for the preparation of a compound of formula (I), as defined in claim 1, or a pharmaceutically acceptable salt thereof, the process comprising reacting a compound of formula (II)

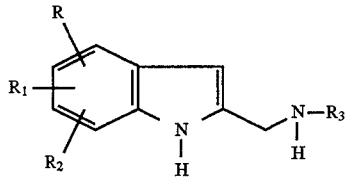

wherein

R, $R_1$, $R_2$ and $R_3$ are as defined in claim 1, with a carbonyl containing cyclizing agent and, if desired, converting a compound of formula (I) into another compound of formula (I), and/or, if desired, converting a compound of formula (I) into a pharmaceutically acceptable salt thereof, and/or, if desired, converting a salt of a compound of formula (I) into a free compound, and/or, if desired, separating a mixture of isomers of a compound of formula (I) into the single isomers.

5. A pharmaceutical composition comprising a suitable carrier and/or diluent and, as an active principle, a compound of formula (I) or a pharmaceutically acceptable salt thereof as defined in claim 1.

6. A compound of formula (II)

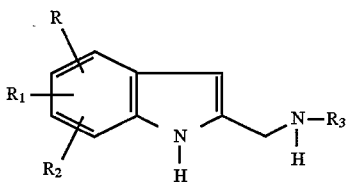

wherein each of R, $R_1$ and $R_2$, which may be the same or different, is hydrogen, halogen, hydroxy, cyano, $C_1$–$C_6$ alkyl, $CF_3$, $C_1$–$C_6$ alkoxy, $C_1$–$C_6$ alkylthio, formyl, $C_2$–$C_6$ alkanoyl, carboxy, $C_1$–$C_6$ alkoxy-carbonyl, nitro, —N($R_4R_5$) in which each of $R_4$ and $R_5$ independently is hydrogen, $C_1$–$C_6$ alkyl, formyl or $C_2$–$C_6$ alkanoyl; or a ($R_6R_7$)N—$SO_2$ group, in which each of $R_6$ and $R_7$ independently is hydrogen or $C_1$–$C_6$ alkyl;

$R_3$ is

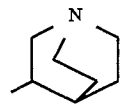

or

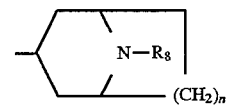

wherein n is integer of 1 or 2 and $R_8$ is hydrogen, $C_1$–$C_6$ alkyl unsubstituted or substituted by phenyl, $C_2$–$C_4$ alkenyl, $C_2$–$C_4$ alkynyl, formyl or $C_2$–$C_6$ alkanoyl.

7. A method of using a compound of formula (I) or a pharmaceutically acceptable salt thereof, according to claim 1, as a $5HT_3$ receptor antagonist.

8. A method of antagonizing $5HT_3$ receptors in a patient in need of such antagonization, comprising administering to the patient a $5HT_3$ receptor-antagonizing effective amount of a compound of formula (I) or a pharmaceutically acceptable salt thereof, according to claim 1.

9. A method of treating a condition selected from the group consisting of anxiety, psychosis, a gut motility disorder, emesis and migraine in a patient in need of such treatment, comprising administering to the patient a condition-treating effective amount of a compound of formula (I) or a pharmaceutically acceptable salt thereof, according to claim 1.

10. A method of treating drug addiction in a patient in need of such treatment, comprising administering to the patient a drug addiction-treating effective amount of a compound of formula (I) or a pharmaceutically acceptable salt thereof, according to claim 1.

11. A method of activating cognition in a patient in need of such activation, comprising administering to the patient a cognition-activating effective amount of a compound of formula (I) or a pharmaceutically acceptable salt thereof, according to claim 1.

* * * * *

UNITED STATES PATENT AND TRADEMARK OFFICE
CERTIFICATE OF CORRECTION

PATENT NO. : 5,637,596
DATED : June 10, 1997
INVENTOR(S) : Varasi, et. al.

It is certified that error appears in the above-identified patent and that said Letters Patent is hereby corrected as shown below: Title page, Item [30], delete " May 24, 1994 " and insert therefor -- May 25, 1994 --.

Column 1, line 25, delete " $C_1$-$c_6$ " and insert therefor -- $C_1$-$C_6$ --.

Column 5, Table II, delete " enthiorinal " and insert therefor -- ēntorhinal --.

Column 5, line 15, delete " ...(8-methyl-B-azabicyclo[3.2.1] " and insert therefor -- (8-methyl-8-azabicyclo[3.2.1] --.

Column 7, line 8, delete "...exo-8-8-azabicyclo " and insert therefor -- exo-8-methyl-8-azabicyclo --.

Column 7, Example 2, in all the compounds reported from line 32 thru line 43, delete " ...aminomethyl- " and insert therefor -- aminomethyl]- --.

Signed and Sealed this

Sixteenth Day of December, 1997

Attest:

BRUCE LEHMAN

*Attesting Officer*   *Commissioner of Patents and Trademarks*